United States Patent
Hudson et al.

(10) Patent No.: US 10,675,222 B2
(45) Date of Patent: Jun. 9, 2020

(54) DRUG DISPENSER ASSEMBLY

(71) Applicant: INTELLIGENT FINGERPRINTING LIMITED, Cambridge (Cambridgeshire) (GB)

(72) Inventors: Mark Hudson, Cambridge (GB); Ulrich Tacke, Kuopio (FI); Antti Törmänen, Forssa (FI); David Russell, Norwich (GB)

(73) Assignee: INTELLIGENT FINGERPRINTING LIMITED, Cambridge (GB)

( * ) Notice: Subject to any disclaimer, the term of this patent is extended or adjusted under 35 U.S.C. 154(b) by 0 days.

(21) Appl. No.: 16/399,093

(22) Filed: Apr. 30, 2019

(65) Prior Publication Data
US 2019/0254930 A1 Aug. 22, 2019

Related U.S. Application Data

(63) Continuation of application No. 15/327,922, filed as application No. PCT/GB2015/052159 on Jul. 24, 2015, now abandoned.

(30) Foreign Application Priority Data

Jul. 24, 2014 (GB) .................................. 1413142.9

(51) Int. Cl.
*A61J 7/00* (2006.01)
*G01N 33/50* (2006.01)
*G06K 9/00* (2006.01)

(52) U.S. Cl.
CPC ........ *A61J 7/0084* (2013.01); *G01N 33/5005* (2013.01); *G06K 9/00033* (2013.01);
(Continued)

(58) Field of Classification Search
CPC ...................... G01N 33/5008; G01N 55/5005
(Continued)

(56) References Cited

U.S. PATENT DOCUMENTS 5,244,815 A * 9/1993 Guirguis .............. A61B 5/1172
436/530
7,766,863 B2 8/2010 Gillespie, Jr. et al.
(Continued)

FOREIGN PATENT DOCUMENTS

CN 101495080 A 7/2009
CN 103536296 A 1/2014
(Continued)

OTHER PUBLICATIONS

A Clark, "Healthcare Global" Magazine, WDM Group, published Dec. 2013, pp. 44-51.

*Primary Examiner* — Timothy R Waggoner
(74) *Attorney, Agent, or Firm* — Lando & Anastasi, LLP

(57) ABSTRACT

A drug dispenser assembly comprising: a drug dispenser for dispensing a drug in a dispense event; and a skinprint analyser configured to receive a skinprint, preferably a fingerprint, of a user. The skinprint analyser is further configured: to perform a verification test regarding the identity of the skinprint; to conduct a chemical analysis for the presence of a metabolite in the skinprint; and to produce data indicative of results of the verification test and the chemical analysis. The drug dispenser assembly further comprises an actuator configured to actuate a dispense event in the event that the results of one or both of the verification test and the chemical analysis meet one or more predetermined conditions.

29 Claims, 4 Drawing Sheets

(52) U.S. Cl.
CPC ....... *G06K 9/00087* (2013.01); *A61J 2200/30* (2013.01); *A61J 2205/40* (2013.01); *A61J 2205/60* (2013.01)

(58) Field of Classification Search
USPC .................................................. 700/231–244
See application file for complete search history.

(56) References Cited

U.S. PATENT DOCUMENTS

| | | | |
|---|---|---|---|
| 2007/0187587 A1* | 8/2007 | Rowell | C01B 33/141 250/288 |
| 2012/0283871 A1 | 11/2012 | Chai et al. | |
| 2012/0316405 A1 | 12/2012 | Taylor | |
| 2013/0218588 A1* | 8/2013 | Kehr | A61B 5/4839 705/2 |

FOREIGN PATENT DOCUMENTS

| | | | |
|---|---|---|---|
| JP | 2011093596 A | 5/2011 |
| WO | 2005043469 A1 | 5/2005 |
| WO | 2008079426 A1 | 7/2008 |
| WO | 2011123931 A1 | 10/2011 |

* cited by examiner

DRUG DISPENSER ASSEMBLY

CROSS-REFERENCE TO RELATED APPLICATIONS

This application is a continuation of pending U.S. patent application Ser. No. 15/327,922, titled DRUG DISPENSER ASSEMBLY and filed on Jan. 20, 2017, which is a U.S. national phase application and claims the benefit of priority under 35 U.S.C. § 371 of PCT/GB2015/052159, titled DRUG DISPENSER ASSEMBLY and filed on Jul. 24, 2015, the contents of each of which are hereby incorporated herein by reference in their entireties for all purposes. Application PCT/GB2015/052159 in turn claims priority to GB1413142.9 filed on Jul. 24, 2014.

BACKGROUND

The importance of maintaining security of drugs and medicines is well known. There may be significant risks associated with a drug being taken by an individual for whom the drug is not intended. Furthermore, there may be significant risks associated with drugs being taken by the intended recipient but at a frequency other than that advised by a medical professional.

STATEMENTS OF INVENTION

Against this background, in a first aspect there is provided a drug dispenser assembly comprising:
 a drug dispenser for dispensing a drug in a dispense event;
 a skinprint analyser configured to receive a skinprint, preferably a fingerprint, of a user and configured:
  (a) to perform a verification test regarding the identity of the skinprint;
  (b) to conduct a chemical analysis for the presence of a metabolite in the skinprint; and
  (c) to produce data indicative of results of the verification test and the chemical analysis; and
 an actuator configured to actuate a dispense event in the event that the results of one or both of the verification test and the chemical analysis meet one or more predetermined conditions.

Advantageously, therefore, this mitigates many risks associated with providing multiple doses of a drug to an individual in a manner that does not restrict access to particular individuals or to particular times (e.g. in accordance with particular dosage regimes). Furthermore, this enables dispensing of the drug only in circumstances where a specific metabolite is detected that may, for example, indicate recent compliance of the user with a particular drug dosage regime.

In a second aspect, there is provided a drug dispenser assembly comprising:
 a drug dispenser configured to perform a plurality of drug dispense events, the drug dispenser comprising a plurality of drug storage locations and being configured such that each drug dispense event dispenses from a different one of the plurality of drug dispense locations;
 a skinprint analyser configured to perform a verification test regarding the identity of the skinprint; and
 a controller configured to actuate a dispense event in the event that:
 (a) the result of the verification test meets a predetermined condition; and
 (b) a timing condition in relation to a dosage regime meets a predetermined value.

Advantageously, therefore, prior to dispensing of a single dose of a drug, both the identity of the recipient and compliance with a dosage regime are confirmed.

In a third aspect, there is provided a method of collecting data regarding a trial of a drug, the method comprising:
 providing a drug dispenser for dispensing a drug in a dispense event;
 providing a skinprint analyser configured to receive a skinprint, preferably a fingerprint;
 using the skinprint analyser to perform a verification test to generate skinprint identification data;
 using the skinprint analyser to conduct chemical analysis for the presence or absence of a metabolite in the skinprint to produce data indicative of results of the chemical analysis;
 actuating a dispense event in the event that one or more than one predetermined condition is met, wherein the one or more than one predetermined condition includes one or more predetermined values for skinprint identification data; and
 transmitting to a server the skinprint identification data and/or data regarding timing of a dispense event.

Advantageously, therefore, there may be confidence that a drug is being dispensed to an intended recipient at an intended time. Furthermore, data regarding the dispensing of the drug may be obtained an analysed in real time.

BRIEF DESCRIPTION OF THE DRAWINGS

A specific embodiment of the invention will now be described, by way of example only, with reference to the following Figures in which.

SPECIFIC DESCRIPTION

Figure 1:
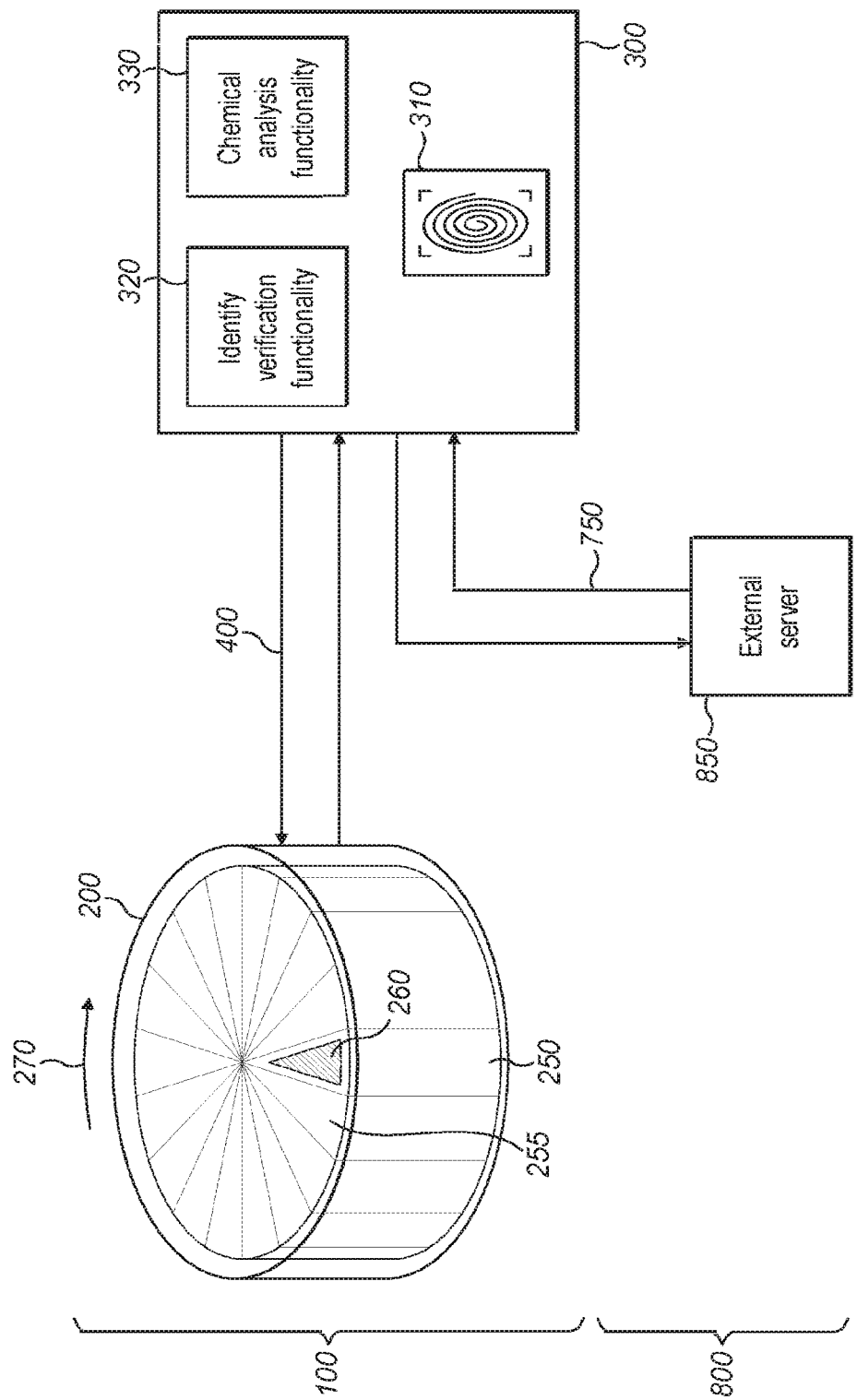
FIG. 1 shows a schematic illustration of the components of a first embodiment of the invention.

FIG. 1 shows a drug dispenser assembly 100 in accordance with a first embodiment of the invention. The drug dispenser assembly 100 comprises a drug dispenser 200, a skinprint analyser 300 and a communication link 400 between the drug dispenser 200 and the skinprint analyser 300. The communication link 400 may be wired, wireless, proprietary, non-proprietary, direct or indirect.

In the FIG. 1 embodiment, the drug dispenser 200 comprises a carousel drug tray 250 and an outer housing 240. The carousel drug tray 250 comprises a plurality of distinct and unconnected compartments 255, each having an opening in a top surface thereof. Each compartment 255 is designed to receive a single dose of a drug. The outer housing 240 comprises an aperture 260. The aperture 260 aligns with an opening of one (only one) of the compartments 255. A user can thereby access the contents of the one single compartment 255 through the aperture 260.

The user is able to access a subsequent dose of the drug only when the carousel drug tray 250 rotates by incrementing such that a single compartment 255 adjacent the previous single compartment 255 aligns with the aperture 260 in the outer housing 240. Rotation of the carousel drug tray 250 may be actuated by an actuator (not shown in FIG. 1) that is inaccessible to the user and that is configured to actuate only on receipt of an actuation signal received from, for example, the skinprint analyser 300. The circumstances and logic relating to actuation are explained in more detail below.

The drug dispenser 200 comprises an actuator (not shown) that triggers, enables or facilitates rotation of the carousel drug tray 250 by a single increment such that the carousel drug tray rotates by an angle equivalent to the angle occupied by a single compartment 255. In this way, a previously enclosed compartment 255 aligns with the aperture 260 such that the contents of said compartment 255 are accessible to a user through the aperture 260.

The skinprint analyser 300 comprises a skinprint substrate 310. In a preferred embodiment, there is a plurality of skinprint substrates 310, each of which is intended only for single use. A stock of skinprint substrates 310 is provided within the skinprint analyser 300 and a fresh skinprint substrate 310 from the stock may be made accessible to the user only in the event of a dispense attempt from the drug dispenser assembly 100. A dispense attempt may be initiated by the user or by a timer or by an externally sourced signal (e.g. from a physician controlled server), or potentially in the event of a combination of more than one of the foregoing.

When a skinprint substrate 310 is made accessible to the user, the user places a skinprint (e.g. a fingerprint) on the skinprint substrate 310, perhaps within a region of the skinprint substrate 310 specifically marked out for this purpose. The skinprint substrate 310 may then be made inaccessible to the user while undergoing testing.

Figure 2:
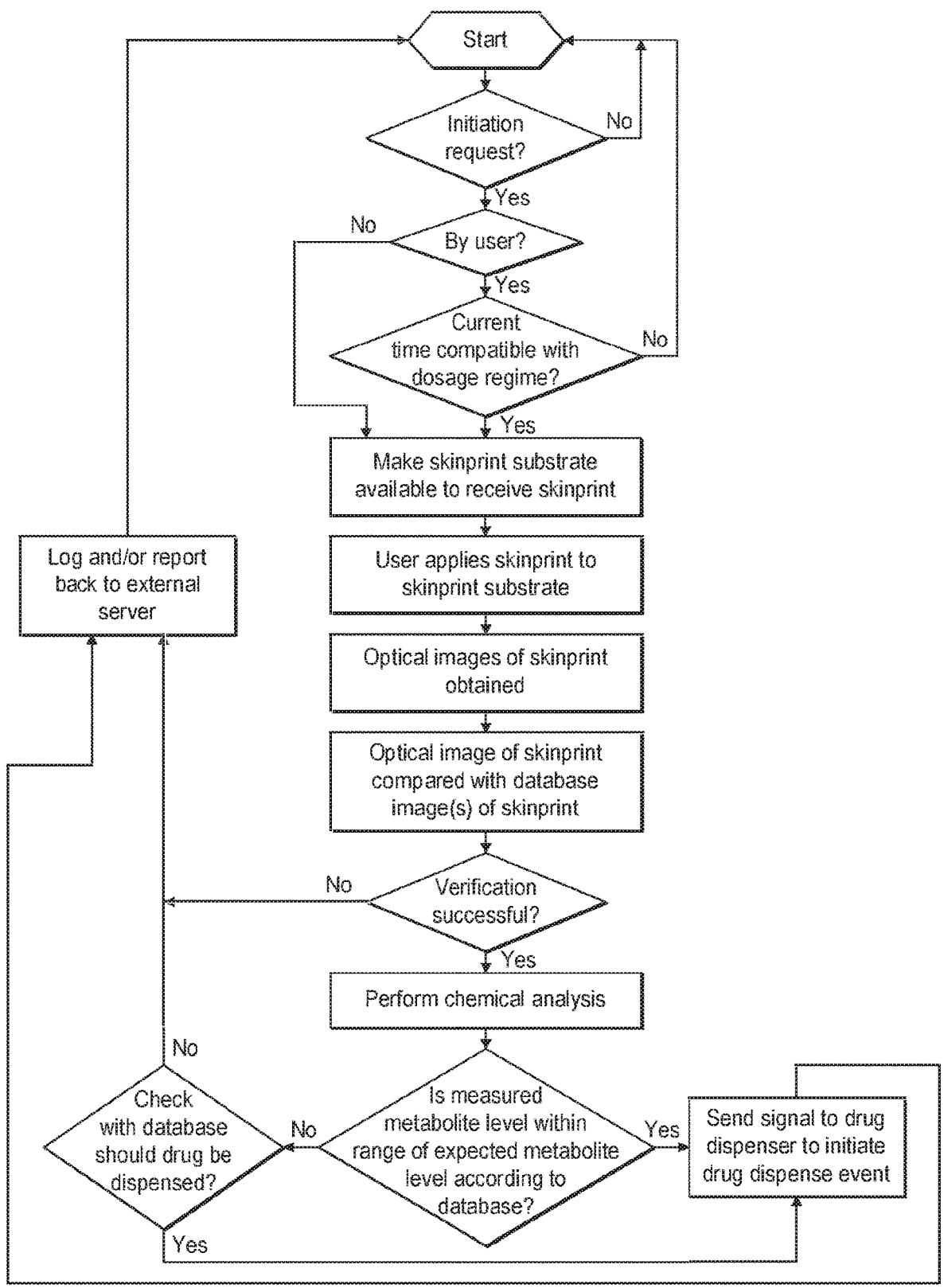
FIG. 2 shows a flow chart illustrating logic that may be applied in executing the first embodiment of the invention.

FIG. 2 shows a sample of the control logic that may be employed in implementing an embodiment of the invention such as that illustrated in FIG. 1.

The analysis of the skinprint on the skinprint substrate 310 involves a first aspect 320, comprising identity verification, and a second aspect 330, comprising chemical analysis. The first and second aspects may be carried out in either order.

The first aspect of analysis comprises obtaining an optical image of the skinprint on the skinprint substrate 310. The optical image is then compared with one or more optical images of skinprints stored in a database. The database may be local to the skinprint analyser or may be on an external server 850, remotely accessed via a data link 750. In the event that the optical image on the skinprint substrate matches successfully with an optical image stored in the database then the identity verification may be considered to be successful. If the optical image on the skinprint substrate does not match successfully with an optical image stored in the database then the identity verification may be considered to be unsuccessful. In the event of unsuccessful identity verification, it may be that no further steps of the procedure take place. Whether or not the identity verification is successful, it may also be that data, including the optical image of the skinprint, may be transmitted securely to the external server 850 via the data link 750.

The second aspect of analysis comprises performing a chemical analysis of substances present in the skinprint. In one embodiment, the chemical analysis may involve applying a reagent solution to the skinprint. The reagent may be chosen to bind with a particular substance that may be present in the skin-print (e.g. a metabolite under test). In the event that the particular substance is present then the reagent will bind with it. In the event that the particular substance is absent then the reagent will not bind with it. The reagent may also comprise a marker, perhaps optically visible or detectable by other means. Whether or not and where the marker is detected can be used to determine whether or not and, if so, to what degree, the substance (e.g. the metabolite) in question is present in the skinprint.

It may be that a specific amount of metabolite (within a range allowing for margins of variation) would be expected to be detected in the skinprint in the event that the user had been complying with a given dosage regime. In such circumstances, the second aspect analysis may include comparing the measured level of metabolite by an expected level of metabolite (wherein the expected level of metabolite may be stored in a database either internal or external to the skinprint analyser 300).

Whether or not the measured level is within a predetermined acceptable margin of the expected level, this may result in data being generated and sent to the external server 850 via the data link 750.

Results of the first and second aspects of the analysis of the skinprint may be fed into a controller (not shown) that compares the results with expected values (either stored in the skinprint analyser 300 or obtained from the external server 850) in order to determine what action to take.

In the event that the results of the first and second aspects of the analysis fall within expected margins, an actuation signal may be transmitted by the controller of the skinprint analyser to the drug dispenser 200 via the communication link 400.

On receipt of the actuation signal by the drug dispenser 200, an actuator (not shown) of the drug dispenser 200 actuates an incremental rotation of the drug tray carousel such that a compartment 255, previously inaccessible and adjacent a previously accessible compartment 255, moves in line with the aperture 260 to become accessible to the user therethrough. The user may then remove the contents of the compartment 255, which may include the drug to be taken by the user.

Further optional additional aspects of the first embodiment will now be described.

The skinprint analyser 300 may further comprise a sensor for obtaining the image of the skinprint. The sensor (not shown) may be a CCD sensor or other optical sensing device. There may also be an illumination source, such as a lamp or LED, for illuminating the skinprint substrate when obtaining the image of the skinprint.

The skinprint analyser 300 may further comprise a radiation source configured to emit radiation of a frequency selected to excite a fluorescent substance that may be present in the reagent. The sensor (not shown) may be configured to detect radiation emitted by a fluorescent substance. Alternatively, there may be a further sensor (not shown) configured especially for this purpose.

The controller may be configured to send and/or receive data from an external source such as the internet, a clinician controller server, a mobile phone or other mobile device, or any other device capable of wired or wireless communication. The sending and/or receiving of data may be encrypted. Access to the controller from an external device (e.g. a clinician controller server) may be subject to complex digital access protection to maximise data security and to minimise the likelihood of a signal to dispense from an unauthorised device being used to actuate a dispense event. The controller may comprise integrated encryption and/or de-encryption functionality.

It may be that, for reasons of data security, no personal data is stored locally on the controller or other aspects of the skinprint analyser 300 or drug dispenser 200. Verification of data (including comparison of an optical image of the skinprint with a database) may take place on an external server (e.g. such as a clinician controlled server).

The drug dispenser assembly 100 may include a transducer such as a button that, when pressed, initiates a user initiated request to the controller. Alternatively, for example, initiation of a user initiated request might be by other means such as, for example, through receipt of a signal via an application from the user's mobile phone. Actuation of the transducer may initiate a control sequence in the controller whereby the controller checks that one or more conditions are met. For example, the controller may check to see that sufficient time has passed since the most recent actuation event, in order to reduce a likelihood of an overdose being taken.

Furthermore, in the event that an appropriate time has passed since the most recent previous actuation event, the controller may initiate a signal to be sent to, for example, an application on the user's mobile phone. In this way, the user may be reminded of the requirement to seek an actuation of dose by complying with the necessary requirements, including providing a skinprint for analysis.

Depending on the specific application, security of the drug dispenser may be of great importance. When referring to security this means providing physical security of the drugs that may be present in the compartments of the drug tray carousel, physical security of the skinprint analyser to reduce unauthorised access to, for example, skinprint substrates, and data security of any data received by or transmitted by the controller or other aspects of the drug dispenser assembly.

Figure 3:
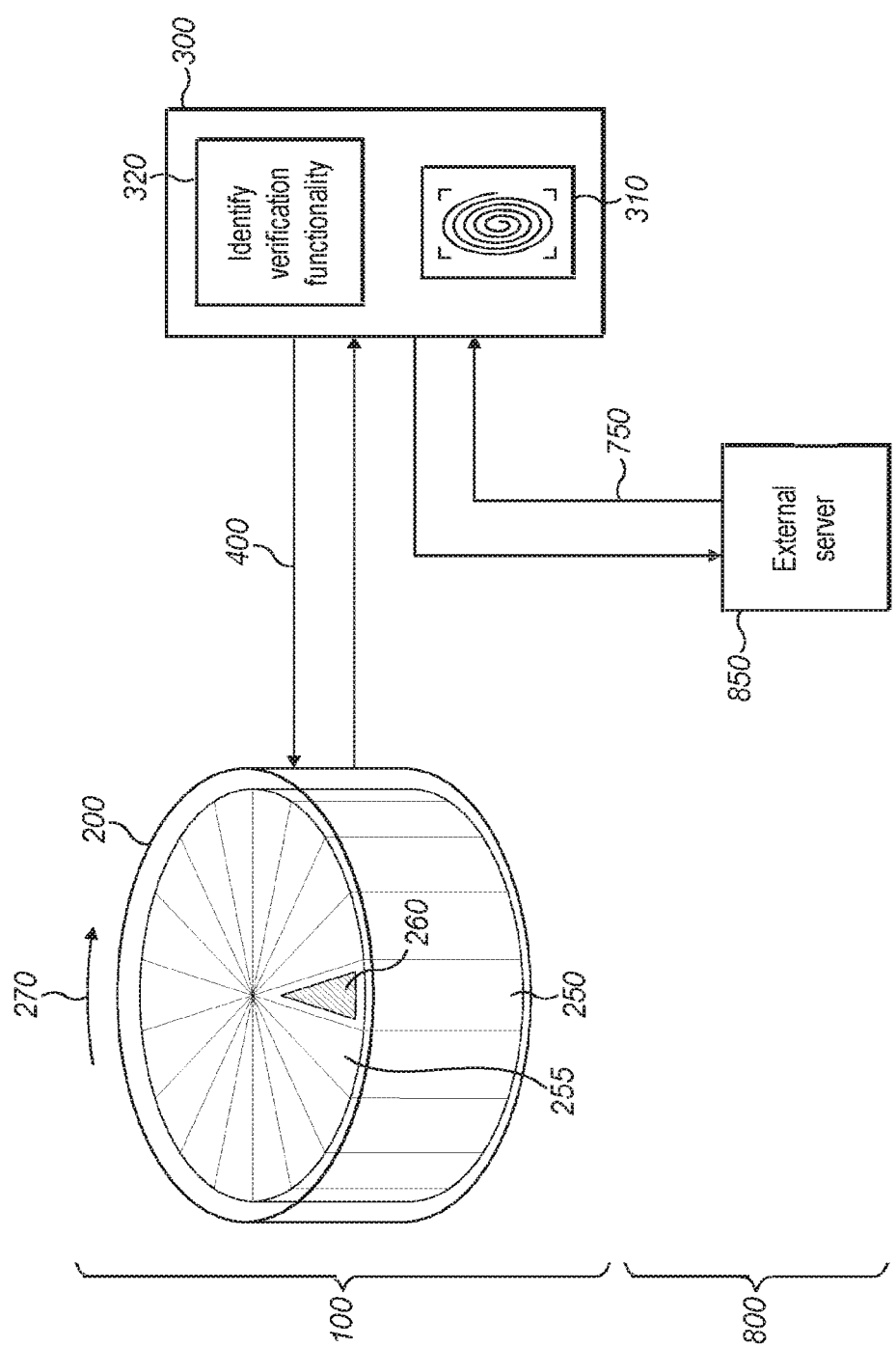
FIG. 3 shows a schematic illustration of the components of a second embodiment of the invention.
Figure 4:
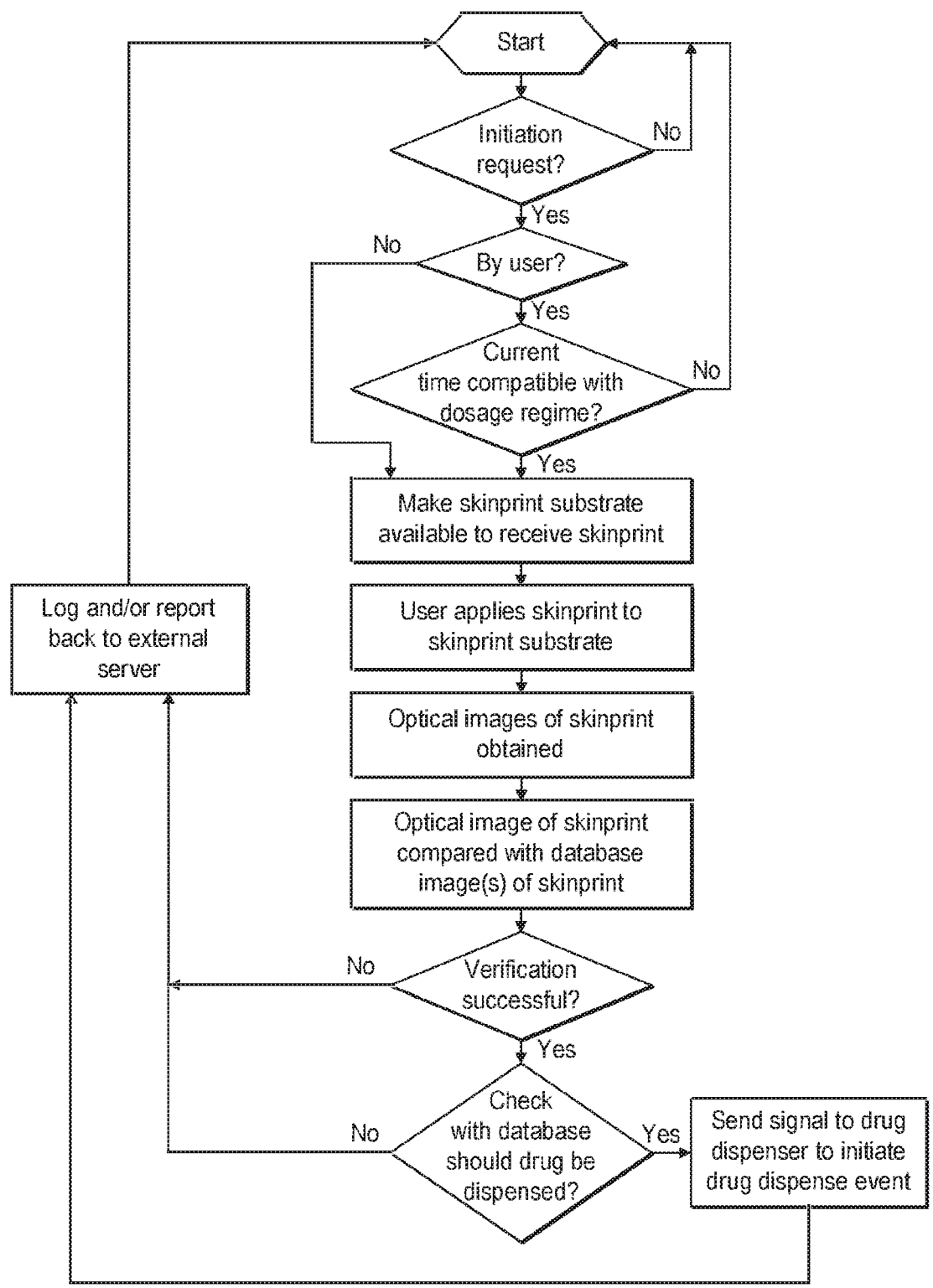
FIG. 4 shows a flow chart illustrating logic that may be applied in executing the second embodiment of the invention.

In a second embodiment of the invention, illustrated in FIGS. 3 and 4, there is provided a drug dispenser assembly that includes the features of the first embodiment except for the chemical analysis functionality. As the skilled person would readily appreciate, in a scenario where chemical analysis is not performed, it is not essential to provide the feature that give rise to that functionality. The second embodiment therefore enables confirmation of the identity of a user and/or confirmation that an appropriate period has passed since a previous dispense event before actuating the next dispense event.

The drug dispenser assembly of either the first or the second embodiment may comprise tamper evident features. For example, there may be aspects of the designed to break in a visually obvious way in the event that access to the drug dispenser carousel, for example, is attempted other than via actuation by the actuator.

In some embodiments, the controller may issue a coupon (perhaps electronically to a user's mobile phone, for example, or by printing one on paper) that the user may exchange, for example, with a retailer. In the event that a paper coupon is issued, the drug dispenser assembly may include a printer for printing the coupon. In this way, the coupon does not exist on paper until it is issued and this reduces a risk of the user attempting to obtain a coupon by tampering with the drug dispenser assembly.

The drug dispenser assembly may include a feature or features that uniquely identify the drug dispenser assembly 100. For example, there may be a serial number etched, engraved, embossed, or printed on the drug dispenser assembly in one or more than one location. In the event that the serial number is printed, it may be printed on an adhesive label with an anti-tamper feature which makes any attempted change visually obvious and/or results in clear damage to the label. Instead or in addition, the drug dispenser assembly 100 may comprise one or more RFID tags or other electronic tags that allow unique identification of the drug dispenser assembly 100.

Data sent to an external server by the controller may include any of the following: date and time information in respect of a dispense attempt; date and time information in respect of a dispense event; total number of dispense attempts; and total number of dispense events; optical image obtained; fluorescent image obtained; chemical analysis results; identify of user as obtained comparing obtained optical image with database; and other information obtained by the device.

In some embodiments, it may be that following a dispense attempt, a clinician is required to log into the clinician controlled server to view data before providing data to be sent to the drug dispenser assembly regarding subsequent control.

In an alternative embodiment, it may be that the aperture 260 by which access to a single compartment 255 is achieved is provided at a lower face of the compartment such that any drug present in the compartment 255 may fall through the aperture when the aperture 260 aligns with the compartment 255. There may then be a conduit through which the drug falls (not shown) so as to provide a distance between the point of dispensing of the drug to the user and the compartment 255 from which the dispensed drug derives.

Moreover, the disclosure is not limited to a drug dispenser of the kind having a carousel drug tray. It may be that the drug is dispensed by other means than a carousel. The skilled person would be aware of alternative drug dispensing means for use with the present invention.

It will be appreciated that many chemistry based techniques for testing for the presence or absence of a particular substance are known and it would be completely clear to the skilled person how they might be implemented in the context of the first embodiment of the present invention. The chemical analysis may involve dissolving the skinprint off its initial position on the substrate or analysing the skinprint in situ on the substrate.

One example application of the drug dispenser assemblies disclosed herein may be in medical trials. In particular, the drug to be dispensed from the drug dispenser assembly may be a drug being trialled by a cohort of individuals. The individuals may be located in a range of locations. Each individual may be provided with their own drug dispenser assembly (potentially a portable embodiment for them to take to their home) or they may have access to a drug dispenser assembly for use by one or multiple individuals that may be located, for example, in a pharmacy, at a medical surgery, at a facility of a drug research organisation, or in any other appropriate location.

For embodiments of drug dispenser assembly that do not have functionality to perform chemical analysis (or for embodiments that do have such functionality), data may be transmitted to an external server (for example, where all the drug trial data is being collected and analysed) regarding identity of the user or users from the fingerprint identity verification test and the times at which the drug has been dispensed to a particular individual.

For embodiments of drug dispenser that have functionality also to perform chemical analysis of the fingerprint, data regarding a metabolite or metabolites detected in the fingerprint by the chemical analysis process may, in addition, be transmitted to an external server (for example, where all the drug trial data is being collected and analysed).

Since the drug dispenser assembly may be configured to dispense only a single dose at each dispense event, the organiser of a drug trial may have increased confidence that a correct dose has been dispensed and may have increased confidence regarding the timings of the doses.

Furthermore, there is the possibility of reducing a burden on the participants of a particular trial by allowing them to actuate a dispense event of a drug from a drug dispenser assembly, perhaps located in their own home, rather than needing to travel to a specific location to receive the dose, or a number of doses for a particular period.

Furthermore, organisers of a drug trial may have greater confidence that participants are complying with the requirements of the trial.

Moreover, in cases where chemical analysis is performed on the skinprint, it reduces (or potentially eliminates) the need for participants to provide a sample of blood or urine in order to detect metabolites that may or may not be present.

Where a number of participants are involved in a drug trial using one or more drug dispenser assemblies of the present disclosure, a statistically significant quantity of data (e.g. clinical data) may be transmitted to a central server. Furthermore, these data may be transmitted and analysed in real time, which gives rise to efficiencies that may not be available in drug trail methodologies that are less automated.

Any of the variations of drug dispenser assembly disclosed herein may be used a drug trial as described.

The invention claimed is:

1. A drug dispenser assembly comprising:
a drug dispenser for dispensing a drug in a dispense event;
a skinprint analyser configured to receive a skinprint, preferably a fingerprint, of a user and configured:
(a) to perform a verification test regarding the identity of the skinprint;
(b) to conduct a chemical analysis for the presence of a metabolite in the skinprint; and
(c) to produce data indicative of results of the verification test and the chemical analysis; and
an actuator configured to actuate a dispense event in the event that the results of one or both of the verification test and the chemical analysis meet one or more predetermined conditions.

2. The drug dispenser assembly of claim 1 wherein the skinprint analyser is configured to accommodate a skinprint substrate for receiving a skinprint of a user.

3. The drug dispenser assembly of claim 2 wherein the skinprint analyser is configured to initiate a supply of a reagent into contact with the skinprint substrate in order to carry out the chemical analysis.

4. The drug dispenser assembly of claim 1 wherein the skinprint analyser further comprises a sensor configured to obtain an image of a skinprint received by the skinprint analyser.

5. The drug dispenser assembly of claim 1 wherein the skinprint analyser further comprises a radiation source configured to emit light for illuminating the skinprint.

6. The drug dispenser assembly of claim 3 wherein the skinprint analyser further comprises a radiation source configured to emit radiation of a frequency selected to excite a fluorescent substance that may be present in the reagent.

7. The drug dispenser assembly of claim 3 wherein the skinprint analyser further comprises one or more sensors configured to sense the presence of visible light and/or radiation emitted by a fluorescent substance that may be present in the reagent.

8. The drug dispenser assembly of claim 1 further comprising a communication link configured to transmit data indicative of the results of one or both of the verification test and the chemical analysis between the skinprint analyser and the actuator.

9. The drug dispenser assembly of claim 8 wherein the communication link is wired or wireless.

10. The drug dispenser assembly of claim 1 wherein the actuator is controlled by a controller.

11. The drug dispenser assembly of claim 10 wherein the controller is configured to instruct the actuator to actuate a dispense event only if:
the result of the verification test confirms the expected identity of the user;
the result of the chemical analysis confirms that an amount of metabolite in the skinprint is within an expected range; and
zero, one or more than one other conditions are met.

12. The drug dispenser assembly of claim 11 wherein the controller is configured to send and/or receive data from an external source, such as the internet.

13. The drug dispenser assembly of claim 11 wherein the one or more than one other conditions include a predetermined time interval having passed since a previous dispense event.

14. The drug dispenser assembly of claim 12, wherein the one or more than one other conditions include receiving an approval signal from the external source.

15. The drug dispenser assembly of claim 11 wherein the one or more than one other conditions include a user initiated request to the controller.

16. The drug dispenser assembly of claim 7 wherein the verification test regarding the identity of the skinprint comprises comparing an image of the skinprint obtained from one or more of the one or more sensors with a stored image of a skinprint.

17. The drug dispenser assembly of claim 16 wherein the stored image is stored by the controller or wherein the stored image is obtained from an external source or database.

18. The drug dispenser assembly of claim 1 further comprising one or more tamper evident features configured to be triggered if an attempt is made to access the drug dispenser and/or the skinprint analyser.

19. The drug dispenser assembly of claim 1 further comprising a coupon dispenser for dispensing a coupon if a set of predetermined conditions is met.

20. The drug dispenser assembly of claim 1 further comprising a tag for identifying uniquely the drug dispenser assembly, wherein optionally the tag is an RFID tag.

21. The drug dispenser assembly of claim 1 further comprising a data recorder, the data recorder configured to record one or more than one of the following:
date and time information in respect of a dispense attempt;
date and time information in respect of a dispense event;
total number of dispense attempts; and
total number of dispense events.

22. The drug dispenser assembly of claim 21 further comprising a data sending controller for sending data in the data recorder to an external location, preferably via a network such as the internet.

23. The drug dispenser assembly of claim 22 wherein the external location is a clinician controlled server.

24. The drug dispenser assembly of claim 23
wherein the actuator is controlled by the controller;
wherein the controller is configured to send and/or receive data from an external source, such as the internet;

wherein the one or more than one other conditions include receiving an approval signal from the external source; and wherein the external source is a clinician controlled server.

25. The drug dispenser assembly of claim 1 further comprising an encryption module configured to encrypt data to be stored and/or sent and to de-encrypt received data.

26. The drug dispenser assembly of claim 1 wherein the drug dispenser comprises a carousel having a plurality of compartments and wherein a dispense event corresponds to a rotation of the carousel so as to increment one compartment.

27. A method of collecting data regarding a trial of a drug, the method comprising:
   providing a drug dispenser for dispensing a drug in a dispense event;
   providing a skinprint analyser configured to receive a skinprint, preferably a fingerprint;
using the skinprint analyser to perform a verification test to generate skinprint identification data;
using the skinprint analyser to conduct chemical analysis for the presence or absence of a metabolite in the skinprint to produce data indicative of results of the chemical analysis;
actuating a dispense event in the event that one or more than one predetermined condition is met, wherein the one or more than one predetermined condition includes one or more predetermined values for skinprint identification data; and
transmitting to a server the skinprint identification data and/or data regarding timing of a dispense event and/or data indicative of results of the chemical analysis.

28. The method of claim 27 wherein the one or more than one predetermined condition includes one or more predetermined values of the data indicative of results of the chemical analysis.

29. The method of claim 28 further comprising using the server to receive data from a plurality of drug dispensers in order to generate a body of data on which statistical analysis is performed.

* * * * *